United States Patent [19]

Hobbs et al.

[11] Patent Number: 5,066,662

[45] Date of Patent: Nov. 19, 1991

[54] SUBSTITUTED OXAZOLIDIN-2-ONES AND 1,2,4-OXADIAZOLIN-5-ONES AND DERIVATIVES THEREOF ACTING AT MUSCARINIC RECEPTORS

[75] Inventors: Sheila H. Hobbs, Dexter; Stephen J. Johnson, Ann Arbor, both of Mich.

[73] Assignee: Warner-Lambert Company, Morris Plains, N.J.

[21] Appl. No.: 526,422

[22] Filed: May 21, 1990

[51] Int. Cl.$^5$ .................... A61K 31/41; C07D 413/06
[52] U.S. Cl. .................... 514/364; 514/252; 514/256; 514/275; 514/304; 514/305; 514/326; 514/340; 514/365; 514/374; 544/238; 544/323; 544/335; 544/336; 546/125; 546/135; 546/209; 546/275; 546/276; 548/132; 548/204; 548/229; 548/232
[58] Field of Search .................... 514/364; 548/132

[56] References Cited

U.S. PATENT DOCUMENTS

| | | | |
|---|---|---|---|
| 2,852,523 | 9/1958 | Lopresti | 548/132 |
| 3,646,024 | 2/1972 | Holdrege | 540/222 |
| 4,193,922 | 3/1980 | Agols | 548/132 |
| 4,309,430 | 1/1982 | Bock et al. | 548/132 |
| 4,804,657 | 2/1989 | Kogure | 548/229 |
| 4,824,838 | 4/1989 | Wachtel | 548/232 |
| 4,897,489 | 1/1990 | Yoshioka et al. | 548/243 |
| 4,943,583 | 7/1990 | Lüthy | 514/340 |
| 4,988,706 | 1/1991 | Hadley et al. | 548/132 |

FOREIGN PATENT DOCUMENTS 1063323 3/1964 United Kingdom ............... 548/132

OTHER PUBLICATIONS

George et al., J. Org. Chem., vol. 41, No. 20, pp. 3233-3237 (1976).
Sumgen et al., Chem. Abstr., vol. 88, Entry 67854 (1978).
Journal of Medicinal Chemistry, 32, pp. 1322-1326 (1989), Sauerberg, P. et al.
Tetrahedron Letters, 30, pp. 2145-2148 (1989), F. B. Gonzales.
Acta Polon. Pharm., 43, pp. 211-217 (1986), Pancechowska-Ksepko, D. et al.
Journal of Heterocyclic Chemistry, 14, pp. 993-996 (1977), Iwao, M. & Kuraishi, T.
*Chimica Acta Turcica*, 4 (1976), Dogan Sumengen, "Synthesis of Some 3-Pyridyl-4-Alkyl-$\Delta^2$-1,2,4-Oxadiazolin-5-Ones and Related Compounds", pp. 191-201.

*Primary Examiner*—Donald G. Daus
*Attorney, Agent, or Firm*—Francis J. Tinney

[57] ABSTRACT

Oxazolidin-2-ones and 1,2,4-oxadiazolin-5-ones substituted in the 4-position of the oxazolidin-2-one ring and the 3-position of the 1,2,4-oxadiazolin-5-one ring with a 5- or 6-member heteroaromatic, a bicyclic heteroaromatic group or a 5- or 6-member heterocyclic group either directly or via a one or two carbon bridge and derivatives thereof are described, as well as methods for the preparation and pharmaceutical compositions of same, which are useful as centrally acting muscarinic agents and are useful as analgesic agents for the treatment of pain, as sleep aids and as agents for treating the symptoms of senile dementia, Alzheimer's disease, Huntington's chorea, tardive dyskinesia, hyperkinesia, mania, or similar conditions of cerebral insufficiency characterized by decreased cerebral acetycholine production or release.

5 Claims, No Drawings

SUBSTITUTED OXAZOLIDIN-2-ONES AND 1,2,4-OXADIAZOLIN-5-ONES AND DERIVATIVES THEREOF ACTING AT MUSCARINIC RECEPTORS

BACKGROUND OF THE INVENTION

The present invention relates to novel substituted oxazolidin-2-ones and 1,2,4-oxadiazolin-5-ones and derivatives thereof useful as pharmaceutical agents, to methods for their production, to pharmaceutical compositions which include these compounds and a pharmaceutically acceptable carrier, and to pharmaceutical methods of treatment. More particularly, the novel compounds of the present invention act at muscarinic receptors and may be useful in treating the symptoms of cognitive decline in an elderly patient.

Disorders of cognition are generally characterized by symptoms of forgetfulness, confusion, memory loss, attentional deficits and/or, in some cases, affective disturbances. These symptoms may arise as a result of the general aging process and/or from organic brain disease, cerebrovascular disease, head injury or developmental or genetic defects.

The general decrease in cognitive function which accompanies the aging process is well accepted. The same phenomenon has been observed and documented in many lower mammals, including those routinely employed in pharmacological testing programs for screening and predicting usefulness for particular drugs in higher animals, including humans.

Although disorders of cognition often accompany the general aging process, presenile and senile primary degenerative dementia are the most common accepted causes of mental deterioration in the elderly. It has been estimated that at least ten percent of persons over sixty years of age will eventually suffer severe mental deterioration. A much larger number will experience cognitive decline of sufficient severity to impede their activities.

Many of the symptoms of cognitive disorders, especially impaired memory, are associated with decreased acetylcholine synthesis and the impairment of cholinoreceptive neurons. In the hippocampus and cerebral cortex of patients suffering from primary degenerative dementia for example, the level of the enzyme choline acetyltransferase (CAT) can be reduced as much as ninety percent (see Davies, P., et al, *The Lancet*, 2, page 1403 (1976); Perry, E. K., et al, *Journal of Neurological Sciences*, 34, pages 247-265 (1977); and White, P., et al, *The Lancet*, 1, pages 668-670 (1977)).

Since CAT catalyzes the synthesis of acetylcholine from its precursors choline and acetyl coenzyme A, the loss of CAT reflects the loss of cholinergic or acetylcholine-releasing nerve endings in the hippocampus and cerebral cortex. There is abundant evidence that cholinergic terminals in the hippocampus are critically important for memory formation.

The cholinergic hypothesis suggests that drugs which restore acetylcholine levels or cholinergic function (i.e., cholinomimetic) are effective in correcting this deficit in neurotransmitter chemical and provide treatment of the memory impairment symptom of cerebral insufficiency. Considerable biochemical, pharmacological, and electrophysiological evidence supports the hypothesis that deficits in the cholinergic system underlie geriatric cognitive dysfunction (Peterson, C. and Gibson, G. E., *Neurobiology of Aging*, 4, pages 25-30 (1983)).

Aged humans and nonhuman primates with decreased cognition show improved memory when they are treated, for example, with acetylcholinesterase inhibitors such as physostigmine. These agents increase the available supply of synaptic acetylcholine by inhibiting its hydrolysis.

Aminopyridines such as 3,4-diaminopyridine ameliorate age-related cognitive deficits by increasing the release of acetylcholine from presynaptic nerve terminals, thus increasing synaptic acetylcholine (see Davis, H. P., et al, *Experimental Aging Research*, 9, pages 211-214 (1983)).

It has been known for some time that the natural alkaloid, muscarine, has the ability to act relatively selectively at autonomic effector cells to produce qualitatively the same effect as acetylcholine. Two other agents, pilocarpine and oxotremorine, have the same principal sites of action as muscarine and acetylcholine and are thus classified as having "muscarinic" action.

It is well known that the cholinergic hypothesis suggests that cholinomimetics, including muscarinic agents, may have potential in treating senile cognitive decline (SCD). However, the multiple development issues associated with cholinomimetics, including, for example, poor bioavailability, short duration of action, and especially parasympathetic side effects, have diminished hopes of adequate therapy with this class of agents.

A series of cyclic carbamate analogs of pilocarpine in which the lactone ring of pilocarpine has been replaced with a 2-oxazolidinone ring has been disclosed by Sauerberg, P., et al (*Journal of Medicinal Chemistry*, 32, pages 1322-1326 (1989)) and Gonzales, F. B., et al (*Tetrahedron Letters*, 30, pages 2145-2148 (1989)).

A series of pyrazine derivatives of the formula

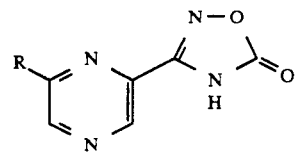

wherein R is H, —OCH3 or

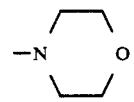

is disclosed by Pancechowska-Ksepko, D., et al, *Acta Polon. Pharm.*, 43, pages 211-217 (1986).

3(2-pyridyl)-1,2,4-oxadiazolin-5-one and 3(2-pyridyl)-4-methyl-1,2,4-oxadiazolin-5-one are disclosed by Iwao, M. and Kuraishi, T., in *Journal of Heterocyclic Chemistry*, 14, pages 993-996 (1977).

3-(3-pyridyl)-1,2,4-oxadiazol-5-one is disclosed in U.S. Pat. No. 3,265,692.

However, none of the compounds disclosed in the aforementioned references suggest the combination of structural variations of the compounds of the present invention described hereinafter. Furthermore, the aforementioned compounds are not disclosed for treating the symptoms of cognitive decline in an elderly patient.

The novel substituted oxazolidin-2-ones and 1,2,4-oxadiazolin-5-ones and derivatives thereof of the present invention which are related to pilocarpine may have high affinity for the muscarinic receptor and thus are expected to be useful in the treatment of the symptoms of cognitive decline in an elderly patient including Alzheimer's disease.

SUMMARY OF THE INVENTION

Accordingly, the present invention is a compound of Formula I

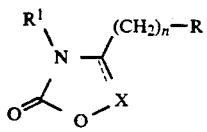

wherein R is selected from the group consisting of

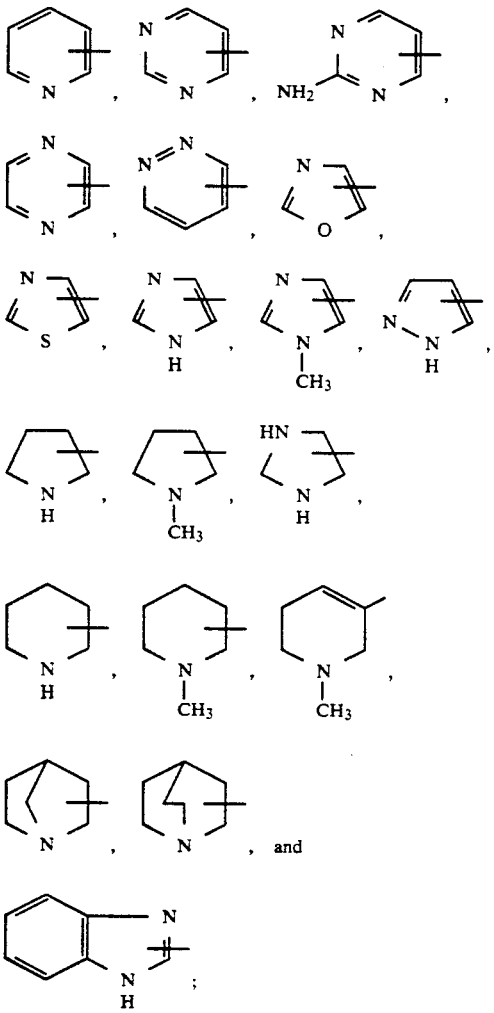

$R^1$ is hydrogen, alkyl of from one to ten carbon atoms, alkynyl of from two to ten carbon atoms or aryl; n is zero or an integer of one or two; X is carbon or nitrogen; and --- represents a single or double bond with the proviso that when, --- represents a double bond X is nitrogen and when --- represents a single bond X is CH$_2$; or a pharmaceutically acceptable acid addition salt thereof; with the exclusion of the compound wherein R is selected from the group consisting of

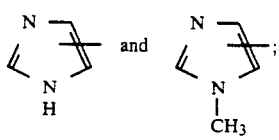

$R^1$ is hydrogen or alkyl of from one to ten carbon atoms; n is one; X is CH$_2$; and --- represents a single bond; and with the further exclusion of the compound wherein R is selected from the group consisting of

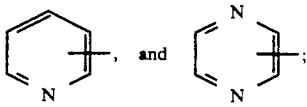

$R^1$ is hydrogen or alkyl of from one to ten carbon atoms; n is zero; X is nitrogen; and --- represents a double bond.

As centrally acting muscarinic agents, the compounds of Formula I are useful as analgesic agents for the treatment of pain in mammals including man, as sleep aids, and as agents for treating the symptoms of senile dementia, Alzheimer's disease, Huntington's chorea, tardive dyskinesia, hyperkinesia, mania or similar conditions of cerebral insufficiency characterized by decreased cerebral acetylcholine production or release.

A still further embodiment of the present invention is a pharmaceutical composition for administering an effective amount of a compound of Formula I in unit dosage form in the treatment methods mentioned above.

Finally, the present invention is directed to methods for production of a compound of Formula I.

DETAILED DESCRIPTION OF THE INVENTION

In the compounds of Formula I, the term "alkyl" means a straight or branched hydrocarbon radical having from one to ten carbon atoms and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl, and the like.

The term "alkynyl" means a straight or branched triple bonded unsaturated hydrocarbon radical having from two to ten carbon atoms and includes, for example, ethynyl, 2-propynyl, 1-butynyl, 2-butynyl, 3-butynyl, 1-pentynyl, 3-pentynyl, 1-hexynyl, 2-hexynyl, 3-hexynyl, 3-heptynyl, 1-octynyl, 2-octynyl, 1-nonynyl, 2-nonynyl, 3-nonynyl, 4-nonynyl, 1-decynyl, 2-decynyl, and the like.

The term "alkoxy" means alkyl-O- of from one to ten carbon atoms as defined above for "alkyl".

The term "thioalkoxy" means alkyl-S- of from one to ten carbon atoms as defined above for "alkyl".

The term "aryl" means an aromatic radical which is a phenyl group or phenyl group substituted by one to four substituents selected from alkyl, alkoxy, thioalkoxy, halogen or trifluoromethyl such as, for example, benzyl, phenethyl, and the like.

"Halogen" is fluorine, chlorine, bromine, or iodine.

Pharmaceutically acceptable acid addition salts of the compounds of Formula I include salts derived from nontoxic inorganic acids, such as hydrochloric, nitric, phosphoric, sulfuric, hydrobromic, hydrochloric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge, S. M., et al, "Pharmaceutical Salts," *Journal of Pharmaceutical Science*, Vol. 66, pages 1-19 (1977)).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free bases for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess asymmetric carbon atoms (optical centers); the racemates as well as the individual enantiomers are intended to be encompassed within the scope of the present invention.

A preferred compound of Formula I is one wherein R is selected from the group consisting of

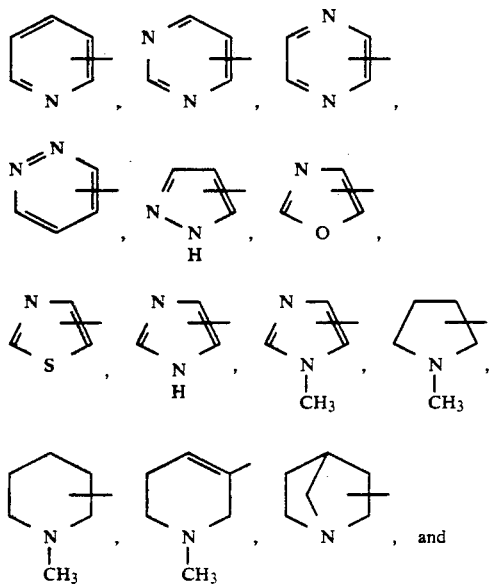

and

n is one; X is nitrogen; and --- represents a double bond.

A more preferred compound of Formula I is one wherein R is selected from the group consisting of

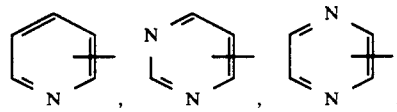

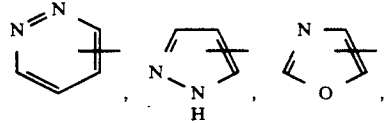

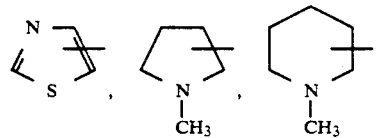

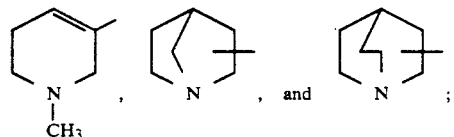

n is one; X is CH$_2$; and --- represents a single bond.

Particularly valuable are:
4-(2-Pyridinylmethyl)-2-oxazolidinone;
4-(4-Pyridinylmethyl)-2-oxazolidinone;
4-(5-Pyrimidinylmethyl)-2-oxazolidinone;
4-(4-Pyrimidinylmethyl)-2-oxazolidinone;
4-(3-Pyridazinylmethyl)-2-oxazolidinone;
4-(4-Pyridazinylmethyl)-2-oxazolidinone;
4-(4-Oxazolylmethyl)-2-oxazolidinone;
4-(5-Oxazolylmethyl)-2-oxazolidinone;
4-(5-Thiazolylmethyl)-2-oxazolidinone;
4-(4-Thiazolylmethyl)-2-oxazolidinone;
4-[(1,2,5,6,-Tetrahydro-1-methyl-3-pyridinyl)-methyl]-2-oxazolidinone;
4-[(1-Azabicyclo[2.2.1]hept-3-yl)methyl]-2-oxazolidinone;
4-[(1-Azabicyclo[2.2.2]oct-3-yl)methyl]-2-oxazolidinone;
3-Methyl-4-(2-pyridinylmethyl)-2-oxazolidinone;
3-Methyl-4-(4-pyridinylmethyl)-2-oxazolidinone;
3-Methyl-4-(5-pyrimidinylmethyl)-2-oxazolidinone;
3-Methyl-4-(4-pyrimidinylmethyl)-2-oxazolidinone;
3-Methyl-4-(3-pyridazinylmethyl)-2-oxazolidinone;
3-Methyl-4-(4-pyridazinylmethyl)-2-oxazolidinone;
3-Methyl-4-(4-oxazolylmethyl)-2-oxazolidinone;
3-Methyl-4-(5-oxazolylmethyl)-2-oxazolidinone;
3-Methyl-4-(5-thiazolylmethyl)-2-oxazolidinone;
3-Methyl-4-(4-thiazolylmethyl)-2-oxazolidinone;
3-Methyl-4-[(1,2,5,6-tetrahydro-1-methyl-3-pyridinyl)-methyl]-2-oxazolidinone;
4-[(1-Azabicyclo[2.2.1]hept-3-yl)methyl]-3-methyl-2-oxazolidinone;

4-[(1-Azabicyclo[2.2.2]oct-3-yl)methyl]-3-methyl-2-oxazolidinone;
3-Ethyl-4-(2-pyridinylmethyl)-2-oxazolidinone;
3-Ethyl-4-(3-pyridinylmethyl)-2-oxazolidinone;
3-Ethyl-4-(4-pyrimidinylmethyl)-2-oxazolidinone;
3-Ethyl-4-(5-pyrimidinylmethyl)-2-oxazolidinone;
3-Ethyl-4-(4-oxazolylmethyl)-2-oxazolidinone;
3-Ethyl-4-(5-oxazolylmethyl)-2-oxazolidinone;
3-Ethyl-4-(3-pyridazinylmethyl)-2-oxazolidinone;
3-Ethyl-4-(4-pyridazinylmethyl)-2-oxazolidinone;
3-Ethyl-4-(5-thiazolylmethyl)-2-oxazolidinone;
3-Ethyl-4-(4-thiazolylmethyl)-2-oxazolidinone;
3-Ethyl-4-[(1,2,5,6-tetrahydro-1-methyl-3-pyridinyl)methyl]-2-oxazolidinone;
4-[(1-Azabicyclo[2.2.1]hept-3-yl)methyl]-3-ethyl-2-oxazolidinone;
4-[(1-Azabicyclo[2.2.2]oct-3-yl)methyl]-3-ethyl-2-oxazolidinone;
3-(2-Pyridinylmethyl)-1,2,4-oxadiazol-5(4H)-one;
3-(4-Pyridinylmethyl)-1,2,4-oxadiazol-5(4H)-one;
3-(5-Pyrimidinylmethyl)-1,2,4-oxadiazol-5(4H)-one;
3-(4-Pyrimidinylmethyl)-1,2,4-oxadiazol-5(4H)-one;
3-(3-Pyridazinylmethyl)-1,2,4-oxadiazol-5(4H)-one;
3-(4-Pyridazinylmethyl)-1,2,4-oxadiazol-5(4H)-one;
3-(4-Oxazolylmethyl)-1,2,4-oxadiazol-5(4H)-one;
3-(5-Oxazolylmethyl)-1,2,4-oxadiazol-5(4H)-one;
3-(5-Thiazolylmethyl)-1,2,4-oxadiazol-5(4H)-one;
3-(4-Thiazolylmethyl)-1,2,4-oxadiazol-5(4H)-one;
3-[(1-Methyl-1H-imidazol-5-yl)methyl]-1,2,4-oxadiazol-5(4H)-one;
3-[(1-Methyl-1H-imidazol-4-yl)methyl]-1,2,4-oxadiazol-5(4H)-one;
3-[(1,2,5,6-Tetrahydro-1-methyl-3-pyridinyl)-methyl]-1,2,4-oxadiazol-5(4H)-one;
3-[(1-Azabicyclo[2.2.1]hept-3-yl)methyl]-1,2,4-oxadiazol-5(4H)-one;
3-[(1-Azabicyclo[2.2.2]oct-3-yl)methyl]-1,2,4-oxadiazol-5(4H)-one;
4-Methyl-3-(2-pyridinylmethyl)-1,2,4-oxadiazol-5(4H)-one;
4-Methyl-3-(4-pyridinylmethyl)-1,2,4-oxadiazol-5(4H)-one;
4-Methyl-3-(5-pyrimidinylmethyl)-1,2,4-oxadiazol-5(4H)-one;
4-Methyl-3-(4-pyrimidinylmethyl)-1,2,4-oxadiazol-5(4H)-one;
4-Methyl-3-(3-pyridazinylmethyl)-1,2,4-oxadiazol-5(4H)-one;
4-Methyl-3-(4-pyridazinylmethyl)-1,2,4-oxadiazol-5(4H)-one;
4-Methyl-3-(4-oxazolylmethyl)-1,2,4-oxadiazol-5(4H)-one;
4-Methyl-3-(5-oxazolylmethyl)-1,2,4-oxadiazol-5(4H)-one;
4-Methyl-3-(5-thiazolylmethyl)-1,2,4-oxadiazol-5(4H)-one;
4-Methyl-3-(4-thiazolylmethyl)-1,2,4-oxadiazol-5(4H)-one;
4-Methyl-3-[(1-methyl-1H-imidazol-5-yl)methyl]-1,2,4-oxadiazol-5(4H)-one;
4-Methyl-3-[(1-methyl-1H-imidazol-4-yl)methyl]-1,2,4-oxadiazol-5(4H)-one;
4-Methyl-3-[(1,2,5,6-tetrahydro-1-methyl-3-pyridinyl)methyl]-1,2,4-oxadiazol-5(4H)-one;
3-[(1-Azabicyclo[2.2.1]hept-3-yl)methyl]-4-methyl-1,2,4-oxadiazol-5(4H)-one;
3-[(1-Azabicyclo[2.2.2]oct-3-yl)methyl]-4-methyl-1,2,4-oxadiazol-5(4H)-one;
4-Ethyl-3-(2-pyridinylmethyl)-1,2,4-oxadiazol-5(4H)-one;
4-Ethyl-3-(4-pyridinylmethyl)-1,2,4-oxadiazol-5(4H)-one;
4-Ethyl-3-(5-pyrimidinylmethyl)-1,2,4-oxadiazol-5(4H)-one;
4-Ethyl-3-(4-pyrimidinylemthyl)-1,2,4-oxadiazol-5(4H)-one;
4-Ethyl-3-(3-pyridazinylmethyl)-1,2,4-oxadiazol-5(4H)-one;
4-Ethyl-3-(4-pyridazinylmethyl)-1,2,4-oxadiazol-5(4H)-one;
4-Ethyl-3-(4-oxazolylmethyl)-1,2,4-oxadiazol-5(4H)-one;
4-Ethyl-3-(5-oxazolylmethyl)-1,2,4-oxadiazol-5(4H)-one;
4-Ethyl-3-(5-thiazolylmethyl)-1,2,4-oxadiazol-5(4H)-one;
4-Ethyl-3-(4-thiazolylmethyl)-1,2,4-oxadiazol-5(4H)-one;
4-Ethyl-3-[(1-methyl-1H-imidazol-5-yl)methyl]-1,2,4-oxadiazol-5(4H)-one;
4-Ethyl-3-[(1-methyl-1H-imidazol-4-yl)methyl]-1,2,4-oxadiazol-5(4H)-one;
4-Ethyl-3-[(1,2,5,6-tetrahydro-1-methyl-3-pyridinyl)methyl]-1,2,4-oxadiazol-5(4H)-one;
3-[(1-Azabicyclo[2.2.1]hept-3-yl)methyl]-4-ethyl-1,2,4-oxadiazol-5(4H)-one; and
3-[(1-Azabicyclo[2.2.2]oct-3-yl)methyl]-4-ethyl-1,2,4-oxadiazol-5(4H)-one; or a pharmaceutically acceptable acid addition salt thereof.

The compounds of Formula I are valuable centrally acting muscarinic agents. The biological activity of compounds of the present invention can be evaluated using a number of tests. The activity of compounds of the present invention as central muscarinic binding site agonists and antagonists can be measured. Thus, in the Receptor [$^3$H]Quinuclidinyl Benzilate Binding Assay (RQNB), described more fully by Watson, M., et al, *Journal of Pharmacology and Experimental Therapeutics*, 237, pages 411 to 418 (1986), rat cerebral cortex tissue is treated with radiolabeled quinuclidinyl benzilate, a known muscarinic binding site antagonist. The concentration of test compound required to inhibit 50% of the binding of this muscarinic antagonist is then determined. This procedure allows a determination of the affinity of the test compounds for the central muscarinic antagonist site. Similarly in the Receptor [$^3$H]Cis-methyldioxalane Assay (RCMD), described more fully by Vickroy, T. W., et al, *Journal of Pharmacology and Experimental Therapeutics*, 229, pages 747 to 755 (1984), rat cerebral cortex tissue is treated with radiolabeled cis-methyldioxalane, a known muscarinic binding site agonist. The concentration of test compound required to inhibit 50% of the binding of this muscarinic agonist is then determined. This procedure allows a determination of the affinity of the test compound for the central muscarinic agonist site.

In the Muscarinic Induced Inositol Phosphate Accumulation Assay (MIPA) human SK-N-SH cells bearing muscarinic binding sites are incubated with the test compound. The production of inositol phosphates is then measured. Stimulation of inositol phosphate turnover reflects the degree of muscarinic agonist activity of the test compound. The concentration of test compound required to produce a response 50% of the maximum is then determined.

A compound of Formula Ia

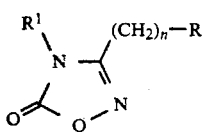

wherein R is selected from the group consisting of

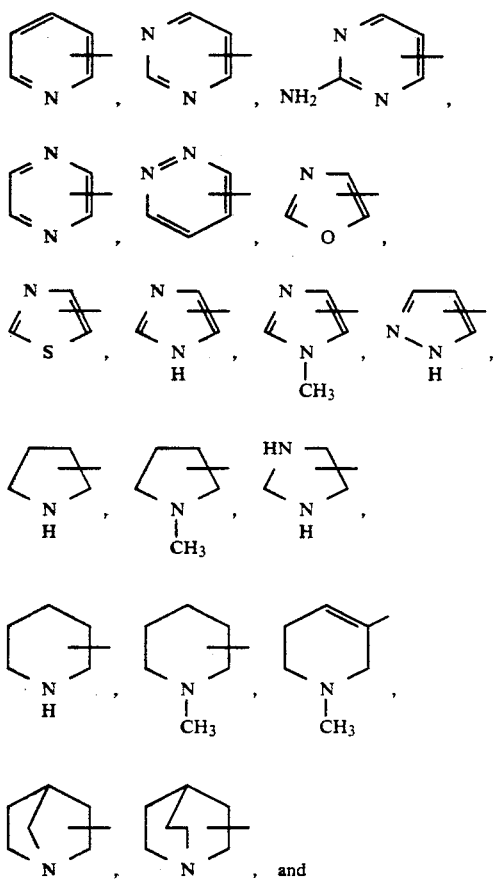

R¹ is hydrogen, alkyl of from one to ten carbon atoms, alkynyl of from two to ten carbon atoms or aryl; n is zero or an integer of one or two; or a pharmaceutically acceptable acid addition salt thereof; with the exclusion of the compound wherein R is selected from the group consisting of

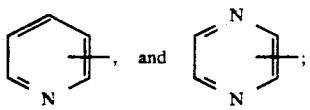

R¹ is hydrogen or alkyl of from one to ten carbon atoms; n is zero; may be prepared by reacting a compound of Formula II

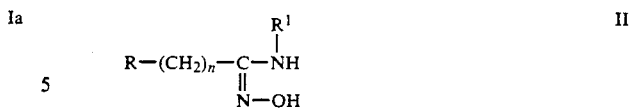

wherein R, R¹, and n are as defined above with a carbonylating reagent such as, for example, 1,1′carbonyldiimidazole, phosgene, and the like to give a compound of Formula Ia.

A compound of Formula Ib

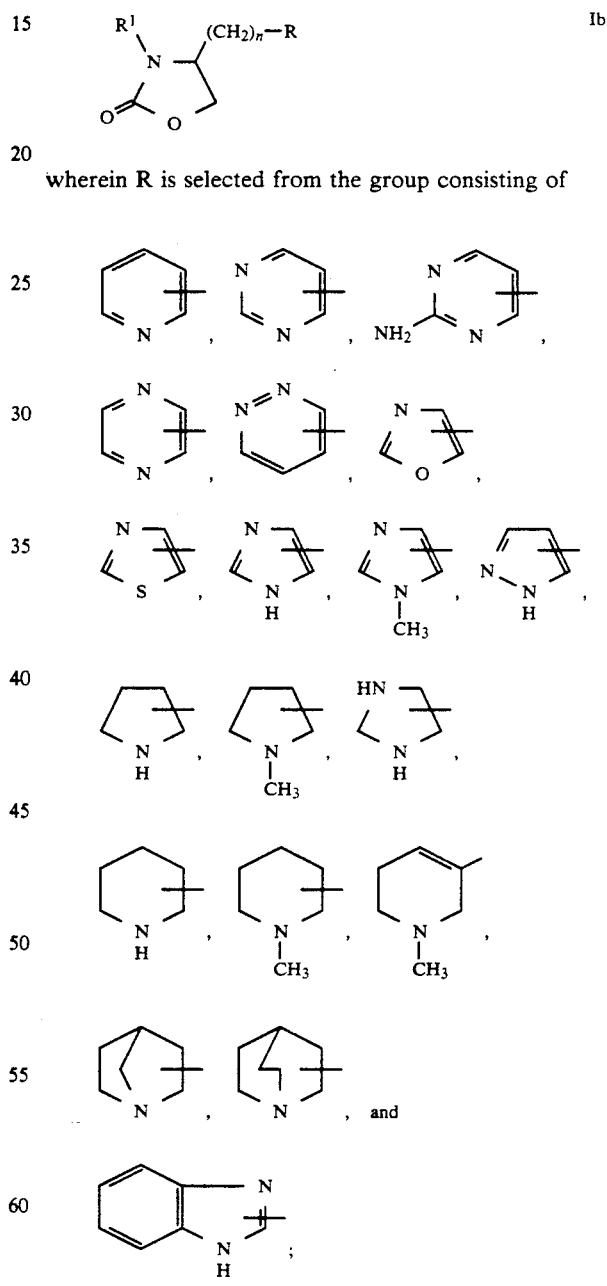

wherein R is selected from the group consisting of

R¹ and n are as defined above; or a pharmaceutically acceptable acid addition salt thereof; with the exclusion of the compound wherein R is selected from the group consisting of

[pyrrole-type structures] and [N-methyl pyrrole-type structure];

$R_1$ is hydrogen or alkyl or from one to ten carbon atoms; n is one; may be prepared by reacting a compound of Formula III $$R-(CH_2)_n-\underset{CH_2OH}{\underset{|}{CH}}-\underset{}{\overset{R^1}{\overset{|}{N}}H}$$     III wherein R, $R^1$, and n are as defined above using the methodology used to prepare a compound of Formula Ia from a compound of Formula II.

A compound of Formula II may be prepared by reacting a compound of Formula IV $$R-(CH_2)_n-\underset{N-OH}{\overset{}{\overset{||}{C}}}-Cl$$     IV wherein R and n are as defined above with ammonia (wherein $R^1$ is hydrogen) or with a compound of Formula $R^{1a}NH_2$, wherein $R^{1a}$ is alkyl of from one to ten carbon atoms, alkynyl of from two to ten carbon atoms, or aryl to give a compound of Formula IV.

A compound of Formula IV may be prepared by reacting a compound of Formula V $$R-(CH_2)_n-\underset{N-OH}{\overset{}{\overset{||}{C}}}-H$$     V wherein R and n are as defined above with chlorine.

A compound of Formula V may be prepared by reacting a compound of Formula VI $$R-(CH_2)_nCHO$$     (VI)

wherein R and n are as defined above with hydroxylamine

A compound of Formula III, wherein $R^1$ is alkyl of from one to ten carbon atoms or alkynyl of from two to ten carbon atoms, and R and n are as defined above may be prepared by reacting a compound of Formula VII $$R-(CH_2)_n-\underset{CO_2R^2}{\underset{|}{CH}}-NHCOR^3$$     VII wherein R is selected from the group consisting of

[pyridine], [pyrazine], [2-aminopyrimidine],

[pyrazine], [pyridazine], [furan-type],

-continued

[thiazole], [imidazole N-H], [N-methyl imidazole], [pyrazole],

[pyrrolidine], [N-methyl pyrrolidine], [piperazine HN],

[piperidine], [N-methyl piperidine], [N-methyl tetrahydropyridine],

[bicyclic amine], [bicyclic amine], and

[indole];

$R^2$ is alkyl of from one to six carbon atoms, $R^3$ is hydrogen, alkyl of from one to nine carbon atoms or alkynyl of from two to nine carbon atoms, and n is as defined above with an organometallic hydride such as, for example, lithium aluminum hydride, and the like to give a compound of Formula III.

A compound of Formula VII may be prepared by reacting a compound of Formula VIII $$R-(CH_2)_n-\underset{CO_2R^2}{\underset{|}{CH}}-NH_2$$     VIII wherein R, $R^2$, and n are as defined above with a compound of Formula IX $$(R^3-CO)_2O$$     (IX)

wherein $R^3$ is as defined above to give a compound of Formula VIII.

A compound of Formula VIII may be prepared by reacting a compound of Formula X $$R-(CH_2)_n-\underset{CO_2H}{\underset{|}{CH}}-NH_2$$     X wherein R and n are as defined above with a compound of Formula XI $$R^2OH$$     (XI)

wherein $R^2$ is as defined above and an acid such as, for example, hydrochloric acid and the like to give a compound of Formula VIII.

A compound of Formula X may be prepared by heating a compound of Formula XII

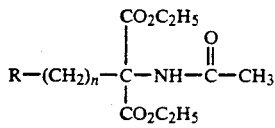

wherein R and n are as defined above with an acid such as, for example, hydrochloric acid and the like to give a compound of Formula X.

A compound of Formula XII may be prepared by ting a compound of Formula XIII

wherein X is halogen and R and n are as defined above with diethyl acetamidomalonate to give a compound of Formula XII.

A compound of Formula XIII may be prepared by reacting a compound of Formula XIV.

where R and n are as defined above with a reagent such as, for example, thionyl chloride, phosphorus trichloride, and the like to give a compound of Formula XIII.

A compound of Formula XIV may be prepared by reacting a compound of Formula XV

wherein R and n are as defined above with an organometallic reagent such as, for example, lithium aluminum hydride and the like to give a compound of Formula XIV.

A compound of Formula III, wherein $R^1$ is hydrogen and R and n are as defined above may be prepared by reacting a compound of Formula VIII with an organometallic hydride such as, for example, lithium aluminum hydride, and the like to give a compound of Formula III.

A compound of Formula III, wherein $R^1$ is aryl and R and n are as defined above may be prepared by reacting a compound of Formula XVI

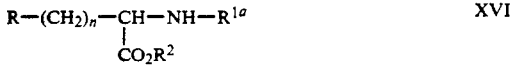

wherein $R^{1a}$ is aryl and R, $R^2$, and n are as defined above using the methodology used to prepare a compound of Formula III, wherein $R_1$ is hydrogen and R and n are as defined above from a compound of Formula VIII.

A compound of Formula XVI is prepared from a compound of Formula XVII.

wherein X is halogen and R, $R^2$ and n are as defined above and a compound of Formula XVIII

wherein $R^{1a}$ is as defined above in the presence of a base such as an organic base, for example, triethylamine and the like or an inorganic base such as sodium acetate and the like to give a compound of Formula XVI.

Compounds of Formula VI, Formula IX, Formula XI, Formula XV, Formula XVII and Formula XVIII are either known or capable of being prepared by methods known in the art.

The compounds of the present invention can be prepared and administered in a wide variety of oral and parenteral dosage forms. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.7 to 7000 mg depending upon the particular application and the potency of the active component. The composition can, if desired, also contain other compatible therapeutic agents.

In therapeutic use as centrally active muscarinic agents the compounds utilized in the pharmaceutical method of this invention are administered at the initial dosage of about 0.01 to about 100 mg per kilogram daily. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following nonlimiting example illustrates the inventors' preferred methods for preparing the compounds of the invention.

EXAMPLE 1

3-Ethyl-4-(4-pyridinylmethyl)-2-oxazolidinone

Step A: Preparation of Methyl 3-i4-pyridinyl)-alanine, dihydrochloride

Diethyl acetamidomalonate (20.0 g, 0.921 mol) is dissolved in 200 mL of absolute ethanol. Sodium metal (4.2 g, 0.1827 mol) is added and the mixture is stirred at room temperature until all of the metal is dissolved. The solution is cooled to 0-5° C. and 13.3 g (0.0811 mol) of 4-picolyl chloride hydrochloride in 100 mL of absolute ethanol is added rapidly. After stirring at room temperature overnight, the mixture is filtered through celite and the filtrate concentrated to a dark oily solid. The residue is dissolved in 200 mL of concentrated hydrochloric acid and refluxed for 4 hours and concentrated in vacuo to a dark oily solid. The residue is dissolved in 200 mL methanol and 2 mL of concentrated hydrochloric acid and refluxed overnight. The solution is concentrated to 16.7 g of orange solid. The hydrochloride salt is purified by trituration with ethanol and ethyl acetate to yield the title compound of a pale yellow solid; mp 180-182° C.

Step B: Preparation of Methyl N-Acetyl-3-(4-pyridinyl)alanine

Methyl-3-(4-pyridinyl)alanine, dihydrochloride (1.4 g, 0.0053 mol) is stirred in dry tetrahydrofuran (20 mL) with acetic anhydride (0.9 mL, 0.0095 mol) and triethylamine (3.3 mL, 0.0233 mol) at room temperature. After stirring at room temperature overnight the mixture is diluted with 20 mL tetrahydrofuran and filtered and the solids washed with tetrahydrofuran. The filtrate is concentrated to a dark oil, dissolved in dichloromethane (50 mL) and washed with dilute sodium bicarbonate solution (50 mL). The organic layer is dried over magnesium sulfate and concentrated. The residue is triturated with diethyl ether, filtered, and dried to afford 0.83 g of the title compound as a tan solid; mp 86-88° C.

Step C: Preparation of α-(Ethylamino)-4-pyridine-propanol

Methyl N-acetyl-3-(4-pyridinyl)alanine (3.68 g, 0.0166 mol) is stirred in dry tetrahydrofuran (200 mL) under a nitrogen atmosphere. Lithium aluminum hydride (44.3 mL of 1.0 M solution in tetrahydrofuran, 0.0443 mol) is added portionwise, noting slight warming. The mixture is heated at reflux for 6 hours and allowed to stand at room temperature overnight. Saturated magnesium sulfate solution is slowly added to the reaction mixture until gas evolution ceases. Stirring is continued until a fine white precipitate forms. The slurry is filtered and the filtrate concentrated to give 2.07 g of the title compound as a golden oil which is used without further purification.

Step D: Preparation of 3-Ethyl-4-(4-pyridinylmethyl)-2-oxazolidinone

Crude α-(ethylamino)-4-pyridinepropanol (2.07 g, 0.0122 mol) is stirred in dry tetrahydrofuran (20 mL) with activated 3Å sieves for about 10 minutes. Carbonyldiimidazole (2.26 g, 0.0139 mol) is added and the mixture is stirred at room temperature overnight. The reaction mixture is concentrated and Kugelrohr distilled at 80-100° C. and 2 mm Hg to remove excess imidazole. The residue is chromatographed on silica gel eluting with 10:1 chloroform:methanol to afford 1.7 g of the title compound as an amber oil.

We claim:

1. A compound of Formula I

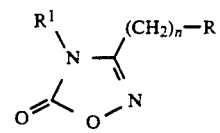

wherein R is selected from the group consisting of

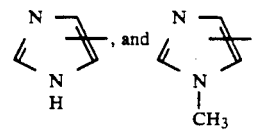

$R^1$ is a hydrogen, alkyl of from one to ten carbon atoms, alkynyl of from two to ten carbon atoms, phenyl or phenyl substituted by one to four substituents selected from C1-C10 alkyl, C1-C10 alkoxy, C1-C10 alkyl thio, halogen or trifluoromethyl; n is zero or an integer of one or two; or a pharmaceutically acceptable acid addition salt thereof.

2. A compound according to claim 1, in which R is selected from the group consisting of

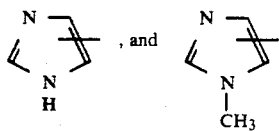

n is one.

3. A compound according to claim 2 selected from the group consisting of:
- 3-[(1-Methyl-1H-imidazol-5-yl)methyl]-1,2,4-oxadiazol-5(4H)-one;
- 3-[(1-Methyl-1H-imidazol-4-yl)methyl]-1,2,4-oxadiazol-5(4H)-one;
- 4-Methyl-3-[(1-methyl-1H-imidazol-5yl)-methyl]-1,2,4-oxadiazol-5(4H)-one;
- 4-Methyl-3-[(1-methyl-1H-imidazol-4-yl)-methyl]-1,2,4-oxadiazol-5(4H)-one;
- 4-Ethyl-3-[(1-methyl-1H-imidazol-5yl)-methyl]-1,2,4-oxadiazol-5(4H-one; and
- 4-Ethyl-3[(1-methyl-1H-imidazol-4-yl)-methyl]-1,2,4-oxadiazol-5(4H)-one; or a pharmaceutically acceptable acid addition salt thereof.

4. A method of treating the symptoms of cognitive decline in an elderly patient comprising administering to a patient suffering therefrom a cholinergically effective amount of a compound according to claim 1.

5. A pharmaceutical composition for the treatment of the symptoms of cognitive decline in an elderly patient comprising administering to a patient suffering therefrom a cholinergically effective amount of a compound according to claim 4 in combination with a pharmaceutically acceptable carrier.